US 12,431,247 B2

(12) United States Patent
Ko et al.

(10) Patent No.: US 12,431,247 B2
(45) Date of Patent: Sep. 30, 2025

(54) SYSTEMS AND METHODS FOR PROGNOSIS PREDICTION OF ACUTE MYELOID LEUKEMIA PATIENTS

(71) Applicant: National Taiwan University, Taipei (TW)

(72) Inventors: Bor-Sheng Ko, Taipei (TW); Yu-Fen Wang, Taipei (TW); Chi-Chun Lee, Hsinchu (TW); Jeng-Lin Li, Hsinchu (TW); Jih-Luh Tang, Taipei (TW)

(73) Assignee: National Taiwan University, Taipei (TW)

( * ) Notice: Subject to any disclaimer, the term of this patent is extended or adjusted under 35 U.S.C. 154(b) by 927 days.

(21) Appl. No.: 16/815,017

(22) Filed: Mar. 11, 2020

(65) Prior Publication Data

US 2021/0287805 A1    Sep. 16, 2021

(51) Int. Cl.
*G16H 50/30*    (2018.01)
*G06N 3/08*    (2023.01)
(Continued)

(52) U.S. Cl.
CPC ............. *G16H 50/30* (2018.01); *G06N 3/08* (2013.01); *G06N 20/10* (2019.01); *G16H 10/40* (2018.01); *G16H 10/60* (2018.01)

(58) Field of Classification Search
None
See application file for complete search history.

(56) References Cited

U.S. PATENT DOCUMENTS

| 2013/0150282 A1* | 6/2013 | Kas ........................ G01N 33/68 |
| | | 506/18 |
| 2016/0125137 A1* | 5/2016 | Ott ......................... G16H 10/60 |
| | | 705/3 |

(Continued)

FOREIGN PATENT DOCUMENTS

WO    WO-2017132749 A1 *    8/2017    ........... C12Q 1/6883

OTHER PUBLICATIONS

Moritz Gerstung et al., Combining gene mutation with gene expression data improves outcome prediction in myelodysplastic syndromes, Nat. Commun. 6, 5901 (2015), https://doi.org/10.1038/ncomms6901 (Year: 2015).*

(Continued)

*Primary Examiner* — Jason B Dunham
*Assistant Examiner* — Nicholas Akogyeram, II
(74) *Attorney, Agent, or Firm* — Perkins Coie LLP; Andrew T. Pettit

(57) ABSTRACT

This application relates generally to a computer implemented method comprising: receiving a medical record data from a patient, wherein said record comprising a static attribute and a time dependent progression attribute; processing the time dependent progression attributes of medical record data using a trained neural network to into time-series representation, and converting the static attributes into static variables; combining the time-series representation and static variables to multiple vectors; providing a prognosis outcome by a trained classifier using said multiple vectors; wherein the neural network is trained by steps of (a) assembling a training data set comprising a retrospective collection of patients' medical record data wherein said record data comprising collected number of static attributes, time dependent progression attributes and patients' mortality and relapse outcomes; (b) processing the time dependent pro-
(Continued)

gression attributes of the training data set using a neural network to convert the time dependent progression attributes into time-series representation; (c) processing the static attributes of the training data set into static variables; and (d) combining the time-series representation and static variables to train a classifier based on the combined time-series representation and static variables.

19 Claims, 5 Drawing Sheets

(51) Int. Cl.
*G06N 20/10* (2019.01)
*G16H 10/40* (2018.01)
*G16H 10/60* (2018.01)

(56) References Cited

U.S. PATENT DOCUMENTS

| | | | |
|---|---|---|---|
| 2019/0034416 A1* | 1/2019 | Al Hasan | G06F 40/56 |
| 2019/0198179 A1* | 6/2019 | Dey | G16H 10/60 |
| 2019/0300956 A1* | 10/2019 | Wang | G16B 25/20 |
| 2019/0378619 A1* | 12/2019 | Meyer | G16H 50/70 |
| 2020/0147136 A1* | 5/2020 | Albertson | A61K 35/17 |
| 2020/0209245 A1* | 7/2020 | Shah | G01N 33/6854 |
| 2020/0337648 A1* | 10/2020 | Saripalli | G06N 3/08 |
| 2021/0020293 A1* | 1/2021 | Richards | G16H 50/30 |
| 2021/0241178 A1* | 8/2021 | Madabhushi | G06N 3/002 |

OTHER PUBLICATIONS

Chih-Chuan Lu, et al. "A BLSTM with Attention Network for Predicting Acute Myeloid Leukemia Patient's Prognosis using Comprehensive Clinical Parameters," Annu. Int. Conf. IEEE Eng. Med. Biol. Soc., 2019: 2455-2458.

DS. Frankel, et al., "Application of Neural Networks to Flow Cytometry Data Analysis and Real-Time Cell Classification," Cytometry, Apr. 1, 1996; 23(4):290-302.

HT. Salah, et al., "Machine learning applications in the diagnosis of leukemia: Current trends and future directions," Int. J. Lab Hematol. Dec. 2019;41(6):717-725.

T. Pham, et al., "Predicting healthcare trajectories from medical records: A deep learning approach," J Biomed. Inform. May 2017; 69:218-229.

* cited by examiner

SYSTEMS AND METHODS FOR PROGNOSIS PREDICTION OF ACUTE MYELOID LEUKEMIA PATIENTS

BACKGROUND

This application relates generally to systems and methods for prognosis prediction of acute myeloid leukemia patients.

Acute Myeloid Leukemia (AML) is the most common type of leukemia disease notoriously known for its poor prognosis outcome, i.e., low survival rate (below 25% in 5 years after diagnosis) and high relapse rate (about 50%). Major clinical treatments rely on intensive chemotherapy and allogeneic hematopoietic stem cell transplantation (HSCT). However, outcomes of the treatment vary greatly from patient to patient; e.g., it is known that younger and healthier patients may extend their remission duration as compared to older patients, and different selections of chemo drugs may result in complete remission (CR) but also risk of mortality. Hence, the prognosis management and treatment plan are often jointly considered in the current clinical setting to handle such potential life-threatening risk for patients while undergoing standard intervention strategy.

SUMMARY

The exemplary embodiments disclosed herein are directed to solving the issues relating to one or more of the problems presented in the prior art, as well as providing additional features that will become readily apparent by reference to the following detailed description when taken in conjunction with the accompanied drawings. In accordance with various embodiments, exemplary systems, methods, devices and computer program products are disclosed herein. It is understood, however, that these embodiments are presented by way of example and not limitation, and it will be apparent to those of ordinary skill in the art who read the present disclosure that various modifications to the disclosed embodiments can be made while remaining within the scope of the invention.

In one aspect provides a computer implemented method comprising: receiving a medical record data from a patient, wherein said record comprising a static attribute and a time dependent progression attribute; processing the time dependent progression attributes of medical record data using a trained neural network to into time-series representation, and converting the static attributes into static variables; combining the time-series representation and static variables to multiple vectors; providing a prognosis outcome by a trained classifier using said multiple vectors; wherein the neural network is trained by steps of (a) assembling a training data set comprising a retrospective collection of patients' medical record data wherein said record data comprising collected number of static attributes, time dependent progression attributes and patients' mortality and relapse outcomes; (b) processing the time dependent progression attributes of the training data set using a neural network to convert the time dependent progression attributes into time-series representation; (c) processing the static attributes of the training data set into static variables; and (d) combining the time-series representation and static variables to train a classifier based on the combined time-series representation and static variables.

In another aspect provides a system, comprising: at least one processor operatively coupled with a datastore, the at least one processor configured to: receive, from a file storage means, a medical record data of a patient, wherein said record comprising a static attribute and a time dependent progression attribute; process the time dependent progression attributes of medical record data using a trained neural network to into time-series representation, and converting the static attributes into static variables; combine the time-series representation and static variables to multiple vectors; provide a prognosis outcome on a display means by a trained classifier using said multiple vectors; wherein the neural network is trained by steps of (a) assembling a training data set comprising a retrospective collection of patients' medical record data from a database wherein said record data comprising collected number of static attributes, time dependent progression attributes and patients' mortality and relapse outcomes; (b) processing the time dependent progression attributes of the training data set using a neural network to convert the time dependent progression attributes into time-series representation; (c) processing the static attributes of the training data set into static variables; and (d) combining the time-series representation and static variables to train a classifier based on the combined time-series representation and static variables.

Yet in another aspect provides a non-transitory computer readable medium has instructions stored thereon, wherein the instructions, when executed by a processor, cause a device to perform operations of the computer implemented methods disclosed herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which;

DETAILED DESCRIPTION OF EXEMPLARY EMBODIMENTS

Figure 1:
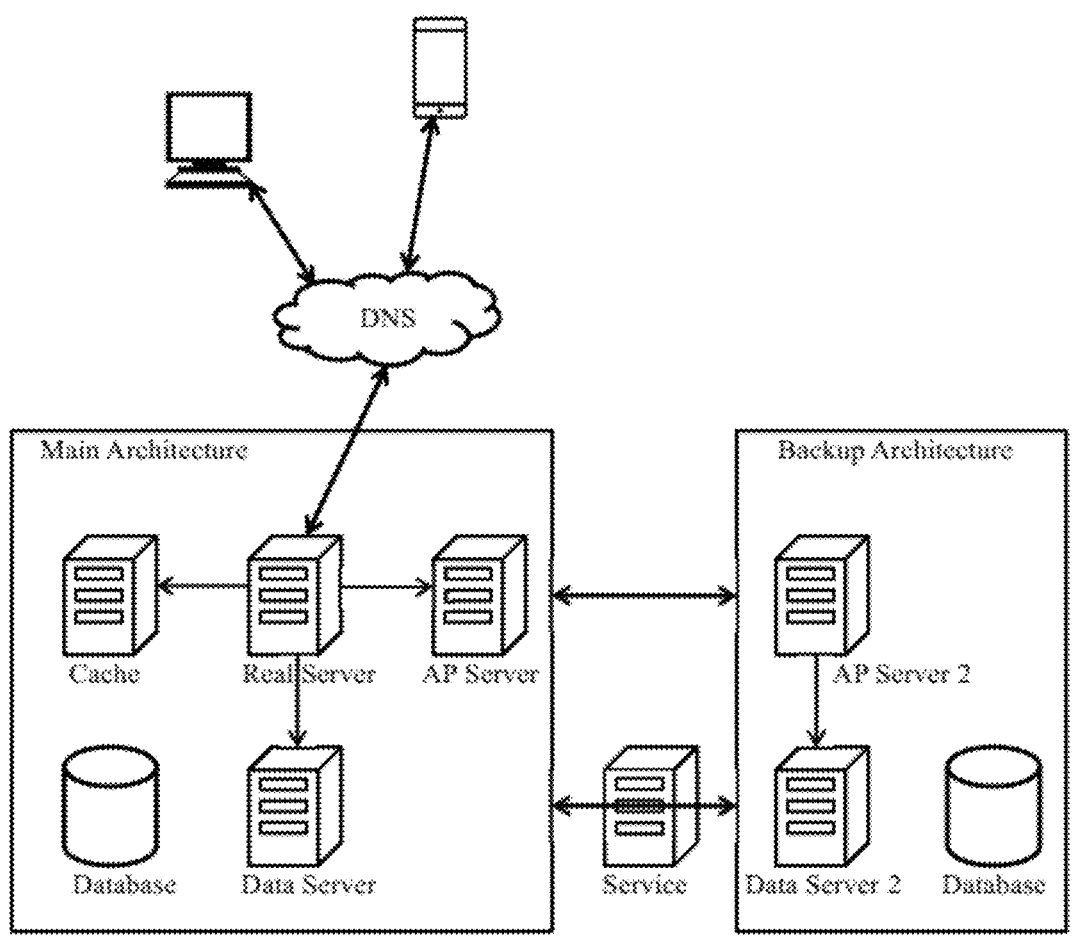
FIG. 1 is a diagram that illustrates an example of a computing architecture.

Forecasting a patient's occurrence of death and relapse over the treatment course is critical and often assessed by the physician based on the patient's prognostic factors. Challenges in obtaining accurate and consistent prognosis management come from issues of complex integrative assessment of heterogeneous and longitudinal clinical variables, including images, laboratory test results, medical records, and even the interviews between patients and doctors. It is further troubled by the occurrences in the variety of treatment outcomes even when receiving similar therapies. Differences in the individual doctor's clinical experiences and the overwhelming clinical parameters available lead to a current situation that there exists no consensus and standard guideline to approach a clinical prognostic decision.

Most of the prior research in prognostic stratification is based on statistical analysis of conventional risk factors, such as demographic, peripheral blood, and cytogenetic. However, such analysis of conventional risk factors is not satisfactory. In order to improve prediction accuracy, researchers have started to explore the use of machine learning techniques. For example, Gupta et al. ("Machine learning prediction of cancer survival: a retrospective study using electronic administrative records and a cancer registry," BMJ open, vol. 4, no. 3, p. e004007, 2014) have used machine learning methods to predict survival rates of various diseases using electronic administrative records. Pan et al. ("Machine learning applications for prediction of relapse in childhood acute lymphoblastic leukemia," Scientific reports, vol. 7, no. 1, p. 7402, 2017) have investigated sociodemographic, clinical, immunological and cytogenetic variables using random forest classifier to predict relapse of acute lymphoblastic leukemia. Recently, Lin et al. ("Application of deep learning on predicting prognosis of acute myeloid leukemia with cytogenetics, age, and mutations," arXiv preprint arXiv: 1810.13247, 2018) have proposed to predict AML patient's diagnosis to death using cytogenetics, age and mutations with a deep learning model. While various works demonstrate promising applications of machine learning for outcome prediction, most if not all of these works consider the patient's clinical variables as static attributes without modeling their temporal aspects, which this invention considers to be key features.

In contrast with the above approaches for AML prognosis stratification, the highly accurate automated AML prognosis systems/methods are provided herein. In some embodiments provide methods and systems of predicting AML patients' outcome in order to address the current clinical challenges in advancing the AML treatments with better prognosis prediction. Such methods and systems, in some embodiments comprise the use of a first neural network to process a time-dependent attribute learned from a retrospective collection of 10-year worth of real patient's comprehensive clinical variables. The invention methods are capable of integrating both static attributes and time-dependent progression of clinical information via an exemplary AI model, e.g., an attention-based BLSTM model. Surprisingly, it outperforms other methods/models without considering temporal aspect. The invention provides a methodological approach in integrating heterogeneous and longitudinal clinical variables that are challenging to be properly modeled using conventional statistical methods.

FIG. 1 illustrates an example of a computing architecture used in the practice of this invention. The main architecture comprises a cache server, a real server, an AP server, a data server, and a database (collectively "a file storage means"). User can access the system from his computer or smartphone (or tablet) to the real server through a computer network or a domain name service (DNS). The real server handles the user's request by processing requests with the cache, the AP server, and the data server. A skilled person in the art would readily recognize other similar or suitable computing architectures in accordance with the practice of the invention.

In accordance with the practice of the present invention there is provided a method to use an exemplary neural network (e.g., attention-based bidirectional long short-term memory, "Att-BLSTM") that is trained with comprehensive aspects (e.g., 5 major dimensions) of clinical variables of an AML patient over his/her treatment course to predict the prognostic outcomes, specifically mortality and relapse. A dataset collected retrospectively from National Taiwan University Hospital over a 10-year window consists of blood tests (e.g., complete blood count (CBC), white blood count (WBC)), medication usages, hematopoietic stem cell transplantation (HSCT) statuses, and gene mutation information was used particularly as time-dependent variables. It is clearly evidenced that an exemplary invention method provides a practical and superb AUC (e.g., 77.1% and 67.3% AUC) for 2-year mortality and relapse prediction and surprisingly similar AUC (e.g., 74.8% and 67% AUC) for 3-month mortality and relapse prediction respectively. The invention provides a longitudinal deep learning approach by using multimodal (e.g., over 5 clinical events' records) to predict AML patient's prognosis outcomes.

In some embodiments provide a computer implemented method comprising: receiving a medical record data from a patient, wherein said record comprising a static attribute and a time dependent progression attribute; processing the time dependent progression attributes of medical record data using a trained neural network to into time-series representation, and converting the static attributes into static variables; combining the time-series representation and static variables to multiple vectors; providing a prognosis outcome by a trained classifier using said multiple vectors; wherein the neural network is trained by steps of (a) assembling a training data set comprising a retrospective collection of patients' medical record data wherein said record data comprising collected number of static attributes, time dependent progression attributes and patients' mortality and relapse outcomes; (b) processing the time dependent progression attributes of the training data set using a neural network to convert the time dependent progression attributes into time-series representation; (c) processing the static attributes of the training data set into static variables; and (d) combining the time-series representation and static variables to train a classifier based on the combined time-series representation and static variables.

Yet in some embodiments provide a system, comprising: at least one processor operatively coupled with a datastore, the at least one processor configured to: receive, from a file storage means, a medical record data of a patient, wherein said record comprising a static attribute and a time dependent progression attribute; process the time dependent progression attributes of medical record data using a trained neural network to into time-series representation, and converting the static attributes into static variables; combine the time-series representation and static variables to multiple vectors; provide a prognosis outcome on a display means by a trained classifier using said multiple vectors; wherein the neural network is trained by steps of (a) assembling a training data set comprising a retrospective collection of patients' medical record data from a database wherein said record data comprising collected number of static attributes, time dependent progression attributes and patients' mortality and relapse outcomes; (b) processing the time dependent progression attributes of the training data set using a neural network to convert the time dependent progression attributes into time-series representation; (c) processing the static attributes of the training data set into static variables; and (d) combining the time-series representation and static variables to train a classifier based on the combined time-series representation and static variables.

Yet in some embodiments provide a non-transitory computer readable medium has instructions stored thereon, wherein the instructions, when executed by a processor, cause a device to perform operations of the computer implemented methods disclosed herein.

In some embodiments, said static attribute comprises basic demographics and first cytogenetics test at diagnosis of said patient. In certain embodiments, said first cytogenetics test is categorized to favorable, intermediate, and adverse risk groups. In certain embodiments, said basic demographics comprise age at diagnosis, and gender of said patient.

In some embodiments, said time dependent progression attribute comprises laboratory results of complete blood count data, white blood cell composition data, gene mutation data, treatment history data, or combinations thereof. In certain embodiments, said time dependent progression attribute comprises laboratory results of complete blood count data, white blood cell composition data, gene mutation data, and treatment history data. In certain embodiments, said treatment history data comprises allogeneic hematopoietic stem cell transplantation (HSCT) and medication history. In certain embodiments, said time dependent progression attribute is processed with a time window of 3, 4, 5, 6, 7, 8, 9, 10, 11, 12, 13, 14, or 14 more days. In certain embodiments, said time dependent progression attribute is processed with a time window of 10 days. In certain embodiments, said time dependent progression attribute is collected within 3 months since patient's diagnosis, or before the patient's complete remission.

Database and Processing

Figure 2:
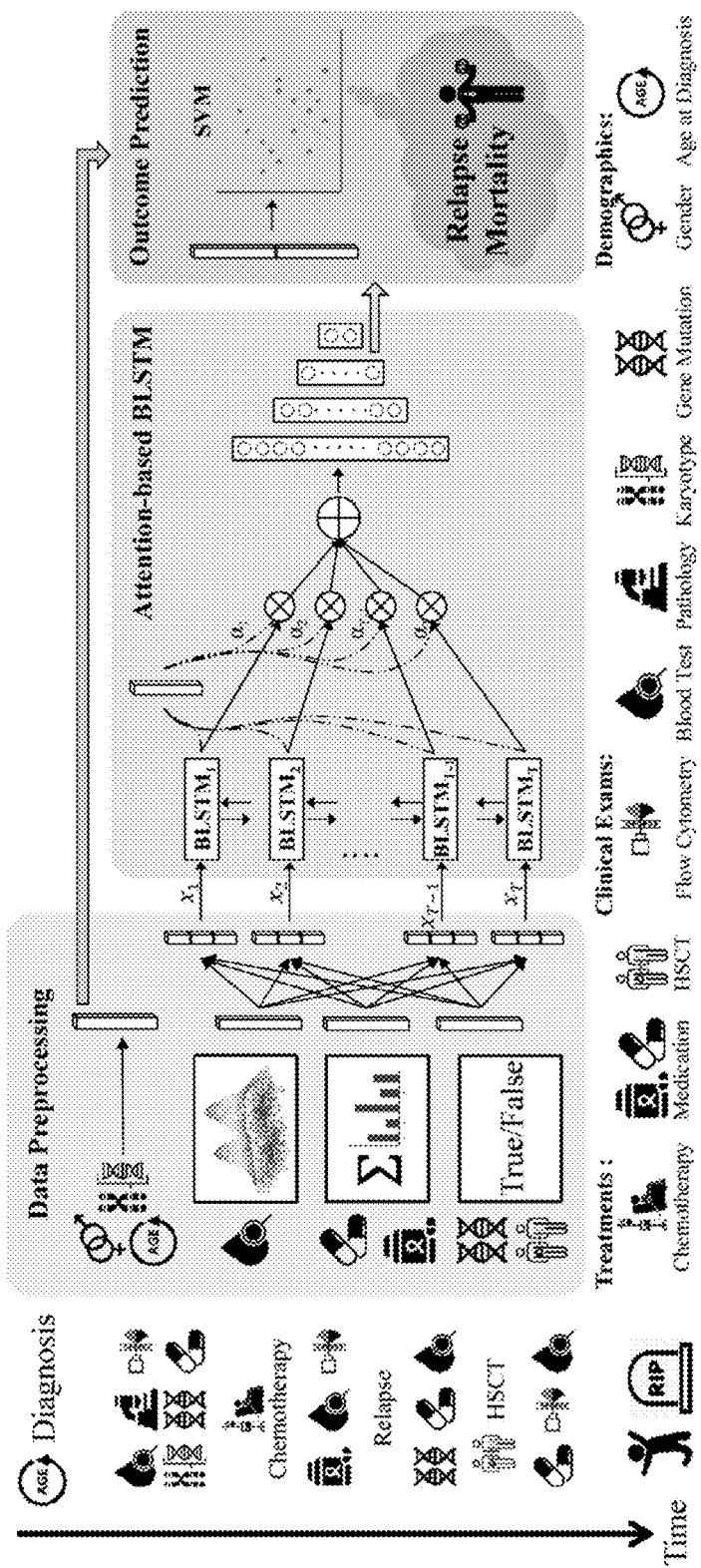
FIG. 2 illustrates an exemplary framework for prognosis prediction of a patient's mortality and relapse using a neural network, an attention-based-bidirectional long short-term memory (Att-BLSTM), in accordance with certain embodiments.
Figure 3:
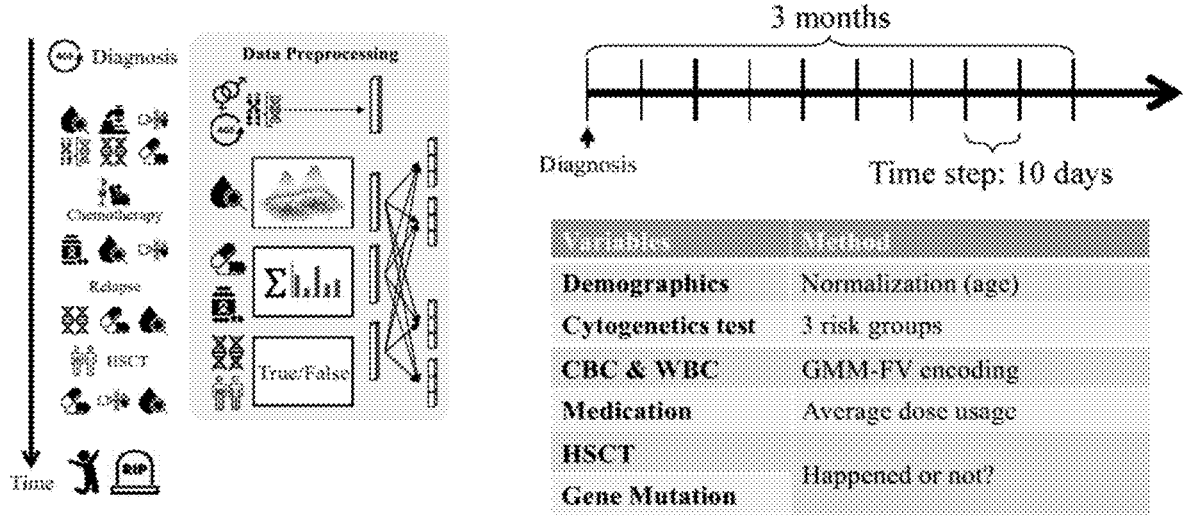
FIG. 3 illustrates an exemplary data preprocessing framework in details.

FIG. 2 illustrates an exemplary methodological framework in accordance with the present invention. The process includes collection of diagnosis data, data preprocessing of said data, then trains an exemplary attention-based AI algorithm such as BLSTM to perform patient AML prognosis prediction, and provides an outcome prediction. In the step of collecting diagnosis data, the retrospective clinical data of AML patients during the periods of January 2006 to February 2017 from the Integrated Medical Database, National Taiwan University Hospital (NTUH-iMD) was collected. There are 637 out of 913 total patients meet the minimal preprocessing requirement, i.e., at least 3 months follow-up duration since diagnosis. FIG. 3 further illustrates the exemplary steps of diagnosis data collection and data preprocessing framework in accordance with the present invention. In accordance with the practice of the invention, the data collection focuses on each patient's personal static and time-dependent attributes. In some embodiments, the personal static attributes include basic demographics (age at diagnosis and gender of the patient), as well as first cytogenetics test at diagnosis. The static attributes like demographics and cytogenetics test are directly taken into used by normalizing according to age and categorized cytogenetics test of 3 risk groups as the input of the variables. The cytogenetics test categorizes each patient into 3 risk groups: favorable, intermediate, adverse. Table I provides the distribution of all static personal features and key treatments and statuses of the data used in the assessment. In other embodiments, time-dependent attributes comprise laboratory results of complete blood count (CBC), white blood cell count (WBC), gene mutation, and treatment history such as allogeneic hematopoietic stem cell transplantation (HSCT) and medication history.

TABLE I

The distribution of key population statistics used in the study.

|   | Total | Gender | | Age at | | | Cytogenetics Risk | | | | C | | Relapse | | HSCT | |
|---|---|---|---|---|---|---|---|---|---|---|---|---|---|---|---|---|
|   |   | M | F | -30 | 30-60 | 60- | Favorabl | Intermedi | Advers | N/A | Y | N | Y | N | Y | N |
| N | 637 | 215 | 322 | 66 | 367 | 204 | 46 | 420 | 107 | 64 | 482 | 155 | 253 | 384 | 462 | 175 |
| % | 100 | 33.8 | 66.2 | 10.7 | 57.6 | 32.4 | 7.2 | 65.9 | 16.8 | 10.0 | 75. | 23.3 | 39.7 | 60.3 | 72.5 | 27.5 |

It is readily recognized by a skilled person in the art that for the time-dependent attributes, each attribute is processed differently to generate features as an input to the Att-BLSTM network. For example, for every certain time window (e.g., 10-day window), termed as a time step, each patient's sequence of the following measured items were gathered and encoded each of them to form a single vector as input. In some embodiments, the time window is 3, 4, 5, 6, 7, 8, 9, 10, 11, 12, 13, 14, or 14 more days. In certain embodiments, the time window is 10 days. In some embodiments, the time window is one day, one week, two weeks, three weeks, one month, or any other suitable time window readily recognized by a skilled person in the art. In some embodiments, the data of each patient within 2, 3, 4, 5, or 6 months since diagnosis or before his/her complete remission is used in the data collection step. In certain embodiments, the data of each patient within 3 months since diagnosis or before his/her complete remission is used in the data collection step and separate the data into 9 time step with duration of 10-day long as shown in FIG. 3.

The summarized description of encoding approach for each item is shown below:

CBC&WBC: The exam result includes 9 and 12 dimensions for CBC and WBC respectively. All available records (i.e., may be different amount for each patient within each time step) were first gathered. Then, for every time step, the sequences of blood test result measurements were encoded into a fixed length vector using a technique based on suitable models such as Gaussian Mixture Model based Fisher-vector encoding (GMM-FV). Please note that other similar encoding model readily recognized by a skilled person in the art would be adapted as well.

Medication: It is based on Anatomical Therapeutic Chemical (ATC) code. For example, there are a total of 30 types of anti-neoplastic medications identified according to L01 and L03 ATC code. The summation of the average dose usage is calculated according these ATC codes within each time step to be used as features. Additionally, ANOVA F-test feature selection is performed to identify the most informative subset of medication-related features. The F-test is used for comparing the factors of the total deviation. Other suitable selection readily recognized by a skilled person in the art may be used to perform to identify the most informative subset of medication-related features.

HSCT: the date of HSCT, and whether relapse occurs after HSCT is noted. Each time step will be given a binary feature value indicating whether the patient has received HSCT and without relapse, i.e., in that particular time step, a value of 1 is given if a patient has gone through HSCT and no relapse has occurred and a value of 0 otherwise.

Gene mutation: The test examines 10 types of genes indicating whether there is mutant. A 10-dimensional feature vector for each time step was generated indicating whether the particular gene type has mutated or not.

Each patient's 3-month worth of data since diagnosis and before first complete remission (CR) was taken as input (resulting in a 9-time-step sequence of feature inputs derived from concatenating the above 5-item time-dependent clinical features vectors) for the relapse outcome prediction tasks. In summary, the preprocessed time-dependent variables are concatenated according to 9 time step and input to a neural network (e.g. the attention-based BLSTM Network) for training. Table II summarizes the key statistics for all static and time-dependent input features.

TABLE II

A summary on the key statistics of the feature set used.

| Characteristics | Dimension | Total | Subset Mortalit | Relapse |
|---|---|---|---|---|
| Patient Number |  | 913 | 637 | 482 |
| Demographic | 2 | 913 | 637 | 482 |
| Cytogenetic | 1 | 2223 | 573 | 488 |
| CBC & WBC | 9 + 12 | 50633 | 11193 | 6314 |
| Medication | 30 | 98519 | 19689 | 10317 |
| HSCT | 1 | 462 | 29 | 30 |
| Gene Mutation | 10 | 1769 | 911 | 657 |

The Use of Neural Network Such as Attention-Based BLSTM Network

In some embodiments, said neural network is support vector machine (SVM), Logistic Regression (LR), Bidirectional Long Short-Term Memory (BLSTM) or attention-based Bidirectional Long Short-Term Memory (attention-based BLSTM) network. In certain embodiments, an exemplary attention based Bidirectional Long Short-Term Memory ("Att-BLSTM") network is utilized to model the sequence of time-dependent feature attributes (converting to the time-dependent vectors). The BLSTM is an improved version of Long Short-Term Memory (LSTM) by considering both forward and backward time-dependent relationship to ensure the temporal gradient can be equally transmitted. The use of attention mechanism can be thought of as having a learnable weight to emphasize the important part of the sequence output from BLSTM. In some embodiments, the attention-based BLSTM uses BLSTM with attention to generate, for each position in an time-dependent output sequence, a set of sub-vector scores that includes a respective sub-vector scores; and generating a position-dependent score-weighted of time-dependent representation.

Outcome Prediction

Once the neural network (e.g., Att-BLSTM network) is trained by a training dataset comprising a retrospective collection of patients' medical record data, the processed time-dependent encoded feature vector can be encoded to generate the representation for each patient from the training dataset or the new patient. Thus, once the neural network (e.g., attention-based BLSTM) is well-trained, the time-series representation by time-dependent variables is generated before network output. The final prediction model is based on training a classifier (e.g., support vector machine, "SVM") with linear kernel by inputting the concatenation of time-series representation and static features from the training dataset. The new patient's prognosis outcome is provided by the trained classifier (e.g., SVM) with the multiple vectors (variables).

In some embodiments, said classifier is SVM, LR, Tree-based classifier, or Deep Neural Network (DNN). In certain embodiments, said classifier is SVM.

In some embodiments, there are two prognosis outcomes as prediction targets: mortality and relapse. The 3-month worth of patient's data was collected since diagnosis date and before first complete remission date to derive the training set features. The prediction target is whether the patient would survive and relapse within the coming N months. The GMM-FV encoding is computed with Gaussian mixture number set to 4. An Adam optimizer with an initial learning rate of 0.00005 was utilized in learning the Att-BLSTM network. The size of mini-batch is 16. Adam is an adaptive learning rate optimization algorithm that's been designed specifically for training deep neural networks.

Two different experiments were conducted. Firstly, the proposed framework in 2-year outcome (i.e., whether the patient would survive or relapse within the next 2 years) prediction tasks with three other methods listed below were compared as well as different input modalities. See FIGS. 4 and 5. Secondly, the accuracy obtained by varying different targeted future prediction periods, i.e., 0-3, 3-12, and 12-24 months was investigated.

SVM: The time-dependent representation is directly concatenated from the encoded features without using Att-BLSTM. Then, this time-dependent representation is concatenated with static features to train a SVM classifier.

LR: It is similar to SVM but the classifier is changed to Logistic Regression (LR).

BLSTM: The time-dependent representation is learned using BLSTM without attention mechanism. Then, the representation is concatenated with static feature to train a SVM classifier.

Att-BLSTM: the preferred framework.

The metric used is unweighted accuracy (UAR) and area under receiver operating characteristic curve (AUC). An exemplary 5-fold patient-independent cross validation scheme was used for all of disclosed experiments herein. In each fold, 80% samples are using as training data, and the rest 20% samples are using to evaluate the performance.

Results

Figure 4:
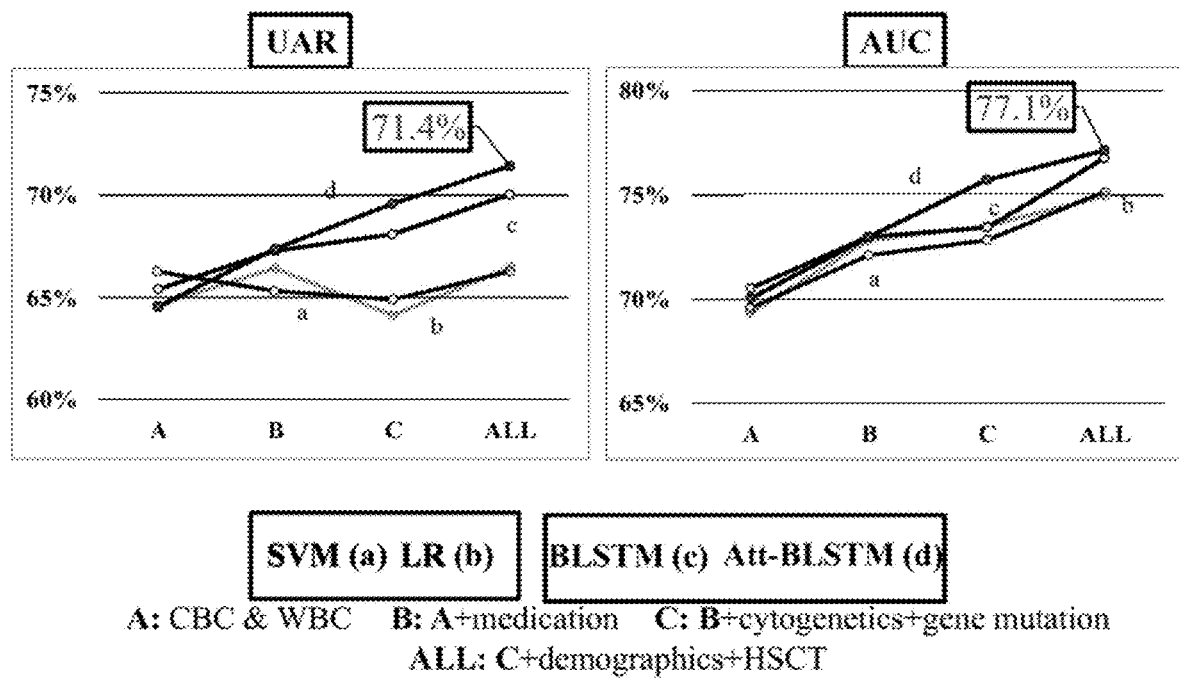
FIG. 4 shows the exemplary mortality results in UAR and AUC by comparing SVM, LR, BLSTM, and Att-BLSTM with different input feature settings: A: CBC&WBC, B: B+medications, C: B+cytogenetics+gene mutation, ALL: C+demographics+HSCT, in accordance with various embodiments.
Figure 5:
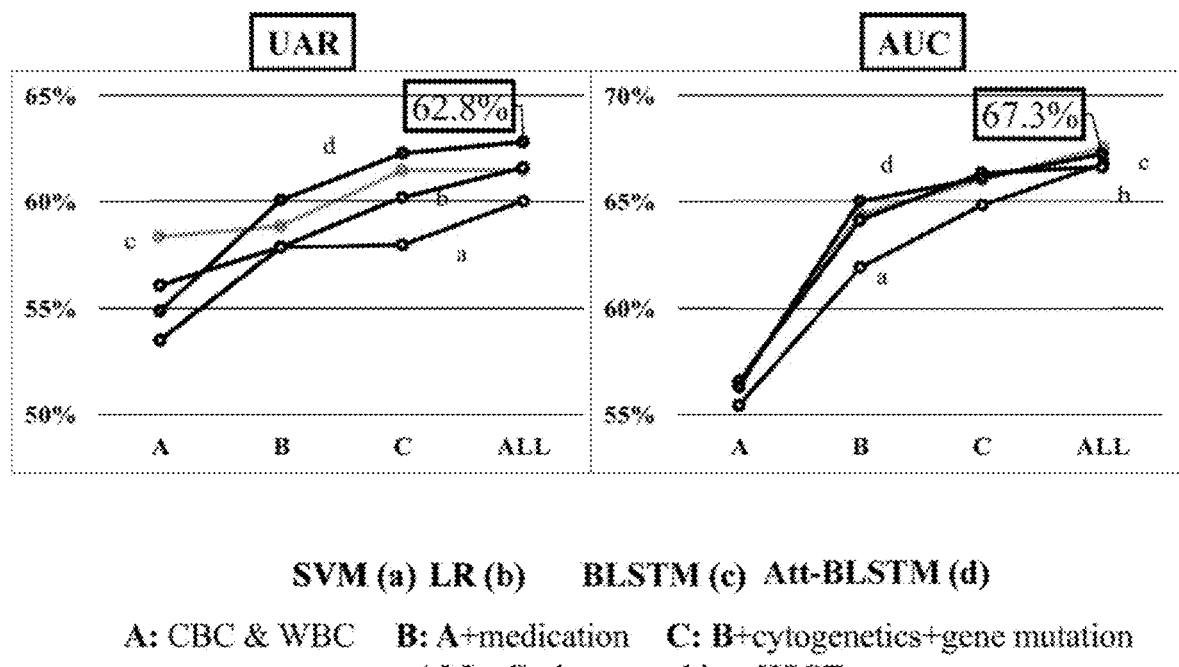
FIG. 5 shows the exemplary relapse results in UAR and AUC by comparing SVM, LR, BLSTM, and Att-BLSTM with different input feature settings: A: CBC&WBC, B: B+medications, C: B+cytogenetics+gene mutation, ALL: C+demographics+HSCT, in accordance with various embodiments.

In one example includes 913 patients in total. Due to the different follow-up duration and treatment condition, there are different numbers of patients included in each experiment. To meet the minimal data requirement, i.e., 3-month follow-up, 637 patients are included, in which 482 patients achieved CR. FIGS. 4 and 5 summarize the accuracy of the first experiment. The proposed method obtains the best accuracy using comprehensive clinical parameters, i.e., all of the input items: 77.1% (AUC) and 71.4% (UAR) for mortality prediction (see FIG. 4) and 67.3% (AUC) and 62.8% (UAR) for relapse prediction (see FIG. 5). By comparing with conventional machine learning methods, i.e., SVM and LR methods, it is clearly evidenced that BLSTM-based network provides a more discriminative representation that learns to predict better on time-series data. Moreover, by further integrating BLSTM with attention mechanism, the prediction accuracy further improves.

In the second experiment, it was found that the proposed framework can not only obtain a better accuracy than other baseline machine learning methods, but also maintain its modeling power when training it with different target prediction periods. Table 3 shows accuracy results obtained for second experiment. The best accuracy occurs when predicting the outcome in the target period of the coming 0 to 3 months: 74.8% (AUC) for mortality and 67.0% (AUC) for relapse. It is noticed that when predicting the patient's outcome in the next 3 to 12 months and 1 to 2 years, the lower accuracy may partly due to the inadequate number of available data that meets the longer follow-up duration requirement. More importantly, various treatments that would occur prior to that target periods but not included in the training features potentially have a larger effect on predicting the patient's final outcome. In some embodiments, the method and system disclosed herein provides 0 to 3 months, 3 to 12 months, or 12-24 months of a prognosis outcome. In certain embodiments, the method and system disclosed herein provides 0-3 months of a prognosis outcome. In certain embodiments, the prognosis outcome is mortality and relapse prediction.

TABLE 3

Results of mortality and relapse prediction in the 0-3, 3-12, and 12-24 months using CBC&WBC, medications, HSCT, and gene mutations, demographics, and cytogenetics

| | | Mortality | | | |
| --- | --- | --- | --- | --- | --- |
| N | Total | Label | | UAR | AUC |
| (Months) | (Samples) | Alive | Death | (%) | (%) |
| 0-3 | 637 | 598 | 39 | 70.1 | 74.8 |
| 3-12 | 597 | 457 | 140 | 65.2 | 71.0 |
| 12-24 | 444 | 367 | 77 | 61.4 | 69.9 |
| | | Relapse | | | |
| N | Total | Label | | UAR | AUC |
| (Months) | (Samples) | Remission | Relapse | (%) | (%) |
| 0-3 | 482 | 443 | 39 | 62.4 | 67.0 |
| 3-12 | 482 | 357 | 125 | 55.6 | 61.3 |
| 12-24 | 482 | 440 | 42 | 56.7 | 62.3 |

Various exemplary embodiments of the invention are described below with reference to the accompanying figures to enable a person of ordinary skill in the art to make and use the invention. As would be apparent to those of ordinary skill in the art, after reading the present disclosure, various changes or modifications to the examples described herein can be made without departing from the scope of the invention. Thus, the present invention is not limited to the exemplary embodiments and applications described and illustrated herein. Additionally, the specific order or hierarchy of steps in the methods disclosed herein are merely exemplary approaches. Based upon design preferences, the specific order or hierarchy of steps of the disclosed methods or processes can be rearranged while remaining within the scope of the present invention. Thus, those of ordinary skill in the art will understand that the methods and techniques disclosed herein present various steps or acts in a sample order, and the invention is not limited to the specific order or hierarchy presented unless expressly stated otherwise.

In various embodiments, the functionality of each of the detection server 106, datastore 108, and local user device 110 may be implemented in a single remote server and/or locally on a user device. In further embodiments, the functionality of each of the flow cytometer 102, detection server 106, datastore 108, and local user device 110 may be implemented in a single flow cytometer and referred to as a combined flow cytometer 116 (e.g., within a single housing). Furthermore, in particular embodiments, each of each of the flow cytometer 102, detection server 106, datastore 108, and local user device 110 may be communicatively coupled with each other directly. Also, the detection server 106, in whole or in part, may be communicatively coupled over the network 114 to a variety of external devices. These external devices may include, for example, the remote user devices 110B and/or remote flow cytometer 112.

While various embodiments of the invention have been described above, it should be understood that they have been presented by way of example only, and not by way of limitation. Likewise, the various diagrams may depict an example architectural or configuration, which are provided to enable persons of ordinary skill in the art to understand exemplary features and functions of the invention. Such persons would understand, however, that the invention is not restricted to the illustrated example architectures or configurations, but can be implemented using a variety of alternative architectures and configurations. Additionally, as would be understood by persons of ordinary skill in the art, one or more features of one embodiment can be combined with one or more features of another embodiment described herein. Thus, the breadth and scope of the present disclosure should not be limited by any of the above-described exemplary embodiments.

It is also understood that any reference to an element herein using a designation such as "first," "second," and so forth does not generally limit the quantity or order of those elements. Rather, these designations can be used herein as a convenient means of distinguishing between two or more elements or instances of an element. Thus, a reference to first and second elements does not mean that only two elements can be employed, or that the first element must precede the second element in some manner.

Additionally, a person having ordinary skill in the art would understand that information and signals can be represented using any of a variety of different technologies and techniques. For example, data, instructions, commands, information, signals, bits and symbols, for example, which may be referenced in the above description can be represented by voltages, currents, electromagnetic waves, magnetic fields or particles, optical fields or particles, or any combination thereof.

A person of ordinary skill in the art would further appreciate that any of the various illustrative logical blocks, modules, processors, means, circuits, methods and functions described in connection with the aspects disclosed herein can be implemented by electronic hardware (e.g., a digital implementation, an analog implementation, or a combination of the two, which can be designed using source coding or some other technique), various forms of program or design code incorporating instructions (which can be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware, firmware or software, or a combination of these technique, depends upon the particular application and design constraints imposed on the overall system. Skilled artisans can implement the described functionality in various ways for each particular application, but such implementation decisions should not be interpreted as causing a departure from the scope of the present disclosure.

Furthermore, a person of ordinary skill in the art would understand that various illustrative logical blocks, modules, devices, components and circuits described herein can be implemented within or performed by an integrated circuit (IC) that can include a general purpose processor, a digital signal processor (DSP), an application specific integrated circuit (ASIC), a field programmable gate array (FPGA) or other programmable logic device, or any combination thereof. The logical blocks, modules, and circuits can further include antennas and/or transceivers to communicate with various components within the network or within the device. A general purpose processor can be a microprocessor, but in the alternative, the processor can be any conventional processor, controller, or state machine. A processor can also be implemented as a combination of computing devices, e.g., a combination of a DSP and a microprocessor, a plurality of microprocessors, one or more microprocessors in conjunction with a DSP core, or any other suitable configuration to perform the functions described herein.

If implemented in software, the functions can be stored as one or more instructions or code on a computer-readable medium. Thus, the steps of a method or algorithm disclosed herein can be implemented as software stored on a computer-readable medium. Computer-readable media includes both computer storage media and communication media including any medium that can be enabled to transfer a computer program or code from one place to another. A storage media can be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to store desired program code in the form of instructions or data structures and that can be accessed by a computer.

In this document, the term "module" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according embodiments of the invention.

Additionally, memory or other storage, as well as communication components, may be employed in embodiments of the invention. It will be appreciated that, for clarity purposes, the above description has described embodiments of the invention with reference to different functional units and processors. However, it will be apparent that any suitable distribution of functionality between different functional units, processing logic elements or domains may be used without detracting from the invention. For example, functionality illustrated to be performed by separate processing logic elements, or controllers, may be performed by the same processing logic element, or controller. Hence, references to specific functional units are only references to a suitable means for providing the described functionality, rather than indicative of a strict logical or physical structure or organization.

Various modifications to the implementations described in this disclosure will be readily apparent to those skilled in the art, and the general principles defined herein can be applied to other implementations without departing from the scope of this disclosure. Thus, the disclosure is not intended to be limited to the implementations shown herein, but is to be accorded the widest scope consistent with the novel features and principles disclosed herein, as recited in the claims below.

What is claimed is:

1. A computer-implemented method for predicting prognosis of a patient that has been diagnosed with acute myeloid leukemia, the method comprising:
    receiving data that is associated with the patient and that comprises
        (i) a first static attribute that is representative of an age or a gender of the patient at diagnosis,
        (ii) a second static attribute that is representative of a categorization for acute myeloid leukemia determined as a result of cytogenetic testing performed at, or subsequent to, diagnosis, and
        (iii) a time-dependent attribute represented as a multi-dimensional vector that indicates, for each of a plurality of genes, whether that gene has mutated or not at each of a plurality of time windows that collectively define an interval of time;
    processing the time-dependent attribute using a trained neural network such that for each of the plurality of time windows, the time-dependent attribute is encoded into a different one of a first plurality of vectors, each of which serves as a time-series representation of a corresponding one of the plurality of time windows;
    converting the first static attribute into a first static variable and the second static attribute into a second static variable;
    concatenating the first plurality of vectors and the first and second static variables to produce a second plurality of vectors, each of which includes (i) a different one of the first plurality of vectors, (ii) the first static variable, and (iii) the second static variable; and
    producing a prognosis outcome for the patient by providing the second plurality of vectors to a trained classifier as input, such that the trained classifier considers the first and second static attributes in combination with each one of the first plurality of vectors in producing the prognosis outcome;
    wherein the trained classifier is trained by steps of
        (a) assembling a training data set comprising a retrospective collection of data of multiple patients that are known to have acute myeloid leukemia, wherein the retrospective collection of data comprises a collected number of static attributes, time-dependent attributes and mortality and relapse outcomes of the multiple patients;
        (b) processing the time-dependent attributes of the training data set using the trained neural network to encode the time-dependent attributes into vectors that serve as time-series representations;
        (c) processing the static attributes of the training data set into static variables; and
        (d) combining the time-series representations and the static variables to train a classifier based on the combined time-series representations and the static variables.

2. The method of claim 1, where the categorization for acute myeloid leukemia determined as the result of the cytogenetic testing is categorized to favorable, intermediate, and adverse risk groups.

3. The method of claim 1, further comprising:
receiving a second time-dependent attribute that indicates complete blood count data, white blood cell composition data, gene mutation data, treatment history data, or combinations thereof, as periodically determined over the interval of time; and
processing the second time-dependent attribute using the trained neural network such that for each of the plurality of time windows, the second time-dependent attribute is encoded into a different one of a third plurality of vectors;
wherein as part of said concatenating, the third plurality of vectors is concatenated with the first plurality of vectors and the first and second static variables.

4. The method of claim 3, wherein said treatment history data comprises allogeneic hematopoietic stem cell transplantation (HSCT) and medication history.

5. The method of claim 3, said time-dependent attribute is collected within 3 months since the patient's diagnosis, or before the patient's complete remission.

6. The method of claim 1, further comprising:
receiving a second time-dependent attribute that indicates complete blood count data, white blood cell composition data, gene mutation data, and treatment history data, as periodically determined over the interval of time; and
processing the second time-dependent attribute using the trained neural network such that for each of the plurality of time windows, the second time-dependent attribute is encoded into a different one of a third plurality of vectors;
wherein as part of said concatenating, the third plurality of vectors is concatenated with the first plurality of vectors and the first and second static variables.

7. The method of claim 1, wherein each time window is 3, 4, 5, 6, 7, 8, 9, 10, 11, 12, 13, 14, or more than 14 days.

8. The method of claim 7, wherein each time window is 10 days.

9. The method of claim 1, wherein the trained neural network is a support vector machine (SVM), Logistic Regression (LR), Bidirectional Long Short-Term Memory (BLSTM) or attention-based Bidirectional Long Short-Term Memory (attention-based BLSTM) network.

10. The method of claim 9, wherein the trained neural network is an attention-based BLSTM.

11. The method of claim 1, wherein the trained classifier is an SVM, LR, Tree-based classifier, or Deep Neural Network (DNN).

12. The method of claim 11, wherein the trained classifier is an SVM.

13. The method of claim 1, wherein said method provides 0 to 3 months of a prognosis outcome.

14. The method of claim 1,
wherein the time-dependent attribute is one of multiple time-dependent attributes in said data,
wherein each of the multiple time-dependent attributes is representative of a different longitudinal clinical variable,
wherein the trained neural network processes each of the multiple time-dependent attributes, so as to produce multiple time-series representations, each of which is combined with the first and second static variables to produce multiple vectors for each of the plurality of time windows, and
wherein the multiple vectors are provided to the trained classifier as input.

15. A system for predicting prognosis of a patient that has been diagnosed with acute myeloid leukemia, the system comprising:
at least one processor operatively coupled with a datastore, the at least one processor configured to:
receive, from a file storage means, data that is associated with the patient and that comprises
(i) a first static attribute that is representative of an age or a gender of the patient at diagnosis,
(ii) a second static attribute that is representative of a categorization for acute myeloid leukemia determined as a result of cytogenetic testing performed at, or subsequent to, diagnosis, and
(iii) a time-dependent attribute that is represented as a multi-dimensional vector that indicates, for each of a plurality of genes, whether that gene has mutated or not at each of a plurality of time windows that collectively define an interval of time;
process the time-dependent attribute using a trained neural network such that for each of the plurality of time windows, the time-dependent attribute is encoded into a different one of a first plurality of vectors, each of which serves as a time-series representation of a corresponding one of the plurality of time windows;
convert the first static attribute into a first static variable and the second static attribute into a second static variable;
combine the first plurality of vectors and the first and second static variables to produce a second plurality of vectors, each of which includes (i) a different one of the first plurality of vectors, (ii) the first static variable, and (iii) the second static variable; and
provide a prognosis outcome for the patient on a display means by providing the second plurality of vectors to a trained classifier as input;
wherein the trained classifier is trained by steps of
(a) assembling a training data set comprising a retrospective collection of data of multiple patients that are known to have acute myeloid leukemia from a database, wherein the retrospective collection of data comprises a collected number of static attributes, time-dependent attributes and mortality and relapse outcomes of the multiple patients;
(b) processing the time-dependent attributes of the training data set using the trained neural network to encode the time-dependent attributes into vectors that serve as time-series representations;
(c) processing the static attributes of the training data set into static variables; and
(d) combining the time-series representations and the static variables to train a classifier based on the combined time-series representations and the static variables.

16. The system of claim 15, wherein said file storage means is a cache server, a real server, an AP server, a data server, and a database.

17. The system of claim 15, wherein the trained neural network is an SVM, LR, BLSTM or attention-based BLSTM network.

18. The system of claim 17, wherein the trained neural network is an attention-based BLSTM.

19. The system of claim 15, wherein the trained classifier is an SVM.

* * * * *